(12) United States Patent
Novelli Rousseau et al.

(10) Patent No.: US 10,704,075 B2
(45) Date of Patent: Jul. 7, 2020

(54) METHOD FOR DETERMINING THE REACTION OF A MICROORGANISM TO ITS EXPOSURE TO A CHEMICAL COMPOUND

(71) Applicants: bioMérieux, Marcy-L'etoile (FR); COMMISSARIAT A L'ENERGIE ATOMIQUE ET AUX ENERGIES ALTERNATIVES, Paris (FR)

(72) Inventors: Armelle Novelli Rousseau, Seyssins (FR); Isabelle Espagnon, Saint Remy les Chevreuse (FR); Quentin Josso, Lyons (FR); Alice Douet, Villebois-lavalette (FR); Frédéric Mallard, Voreppe (FR); Olivier Gal, Montrouge (FR)

(73) Assignees: BIOMÉRIEUX, Marcy-L'Etoile (FR); COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 24 days.

(21) Appl. No.: 15/779,295

(22) PCT Filed: Nov. 25, 2016

(86) PCT No.: PCT/FR2016/053100
§ 371 (c)(1),
(2) Date: May 25, 2018

(87) PCT Pub. No.: WO2017/089727
PCT Pub. Date: Jun. 1, 2017

(65) Prior Publication Data
US 2018/0355399 A1     Dec. 13, 2018

(30) Foreign Application Priority Data
Nov. 27, 2015 (FR) .................................. 15 61446

(51) Int. Cl.
*G01N 21/65* (2006.01)
*G01N 33/569* (2006.01)
*C12N 11/00* (2006.01)
*C12Q 1/18* (2006.01)

(52) U.S. Cl.
CPC ............... *C12Q 1/18* (2013.01); *G01N 21/65* (2013.01); *G01N 33/56911* (2013.01); *C12N 11/00* (2013.01)

(58) Field of Classification Search
None
See application file for complete search history.

(56) References Cited

U.S. PATENT DOCUMENTS

| | | | | |
|---|---|---|---|---|
| 6,884,582 B1* | 4/2005 | Chaton | ............... | C12Q 1/6816 422/82.05 |
| 8,187,820 B2* | 5/2012 | Chau | ............ | B82Y 15/00 435/7.1 |
| 8,519,358 B2* | 8/2013 | Ingber | ................ | G01N 21/0303 250/458.1 |
| 10,073,036 B2* | 9/2018 | Ingber | ................ | G01N 21/0303 |
| 10,253,002 B2* | 4/2019 | Page | ...................... | A61K 45/06 |
| 10,255,688 B2* | 4/2019 | Perraut | .............. | G01N 15/1434 |
| 10,458,897 B2* | 10/2019 | Perraut | ................ | G03H 1/0005 |
| 2005/0123917 A1 | 6/2005 | Labischinski et al. | | |

(Continued)

FOREIGN PATENT DOCUMENTS

| | | | | |
|---|---|---|---|---|
| EP | 2331970 A1 * | 6/2011 | ......... | G01N 33/5082 |
| WO | 03042406 A2 | 5/2003 | | |

(Continued)

OTHER PUBLICATIONS

Baritaux et al, Imaging, Manipulation, and Analysis of Biomolecules, Cells, and Tissues XIII; Progress in Biomedical Optics and Imaging—Proceedings of SPIE (2015), vol. 9328, am: 932811 Editor Farkas et al (Year: 2015).*

(Continued)

*Primary Examiner* — Nita M. Minnifield
(74) *Attorney, Agent, or Firm* — Cantor Colburn LLP

(57) ABSTRACT

The invention concerns a method for determining the reaction of at least one bacterium of interest to its exposure to an antibiotic implementing a Raman spectroscopy analysis comprising the following steps:

Having a biological sample that could contain said bacteria of interest,

Preparing at least two fractions of said sample each comprising one or more living bacteria of interest, Capturing, in each fraction, at least one living bacterium of interest by using a binding partner, Exposing at least one of the fractions to at least one concentration of at least one given antibiotic, the other of the fractions being the control fraction, Submitting the bacterium/bacteria of interest contained in the fractions to an incident light and analyzing the resultant light obtained by Raman diffusion by the bacterium/bacteria of interest by Raman spectroscopy in order to obtain as many Raman spectra as bacteria, Treating said spectra in order to obtain a signature of the reaction of the or each bacterium/bacteria of interest to the exposure to said antibiotic and of the control, Comparing the signature obtained accordingly per bacterium of interest to a reference base defined under the same conditions as above, for different bacteria and at least said antibiotic, and Defining a sensitivity clinical profile of said bacterium of interest to said antibiotic.

20 Claims, 6 Drawing Sheets

(56) References Cited

U.S. PATENT DOCUMENTS

| | | | | |
|---|---|---|---|---|
| 2008/0220465 | A1* | 9/2008 | Ingber | G01N 33/9446 435/32 |
| 2011/0256578 | A1* | 10/2011 | Chau | B82Y 15/00 435/29 |
| 2012/0129707 | A1* | 5/2012 | Wang | G01N 33/54353 506/9 |
| 2013/0052636 | A1 | 2/2013 | Verma et al. | |
| 2015/0024403 | A1* | 1/2015 | Szalay | C12Q 1/6897 435/7.4 |
| 2017/0074798 | A1* | 3/2017 | Ingber | G01N 21/0303 |
| 2018/0195964 | A1* | 7/2018 | Ingber | G01N 21/6486 |
| 2018/0355399 | A1* | 12/2018 | Novelli Rousseau | C12Q 1/18 |
| 2019/0017090 | A1* | 1/2019 | Ben-David | C12Q 1/18 |
| 2019/0086866 | A1* | 3/2019 | Douet | C12Q 1/20 |

FOREIGN PATENT DOCUMENTS

| | | | | |
|---|---|---|---|---|
| WO | WO-03042406 | A2 * | 5/2003 | C12Q 1/18 |
| WO | WO-2010026218 | A1 * | 3/2010 | G01N 33/5082 |
| WO | WO-2011047662 | A2 * | 4/2011 | G01N 21/658 |
| WO | WO-2012068226 | A2 * | 5/2012 | G01N 33/54353 |
| WO | 2013093913 | A1 | 6/2013 | |
| WO | WO-2013093913 | A1 * | 6/2013 | G01N 21/65 |
| WO | WO-2017089727 | A1 * | 6/2017 | C12Q 1/18 |
| WO | WO-2017207184 | A1 * | 12/2017 | C12Q 1/20 |

OTHER PUBLICATIONS

Charretier et al, Scientific Reports, 2015, 5:13944, 12 pages. published: Sep. 9, 2015 (Year: 2015).*

Douet et al, Biophotonics: Photonic Solutions for Better Health Care V; Proceedings of SPIE—The International Society for Optical Engineering (2016), vol. 9887, am: 98871W, 22 refs. abstract only (Year: 2016).*

Espagnon et al. Journal of Biomedical Optics 19(2), 027004 (Feb. 2014). published online: Feb. 12, 2014 (Year: 2014).*

Munchberg et al, Anal Bioanal Chem (2014) 406:3041-3050. published online: Mar. 21, 2014 (Year: 2014).*

Ulrich-Christian et al, Integrated Research and Treatment Center "Center for Sepsis Control and Care" (CSCC), Germany and Institute of Photonic Technology, Jena University Hospital, Jena, Germany. Optik & Photonik, 2013, 8/4:36-39. Abstract only (Year: 2013).*

Novelli-Rosseau et al, Scientific Reports. 2018, 8:3957, 13 pages. published online: Mar. 2, 2018 (Year: 2018).*

Schroder et al, Infection, Supplement, (Aug. 2013) vol. 41, No. 1, Supp. SUPPL. 1, pp. S35-S36. Abstract No. 036. Editor: Brunkhorst et al. Abstract only (Year: 2013).*

Schroder et al, Anal. Chem. 2013, 85, 10717-10724. published Oct. 14, 2013 (Year: 2013).*

Schultz et al, Proc. SPIE 8939, Biomedical Vibrational Spectroscopy by Raman Advances in Research and Industry, 89390D (Mar. 4, 2014), 15 pages. (Year: 2014).*

Strola et al, Journal of Biomedical Optics 19(11), 111610 (Nov. 2014). published online: Jul. 16, 2014 (Year: 2014).*

Strola et al, Proc. of SPIE 2014. vol. 8939, 893905-1. 10 pages, (Year: 2014).*

Walter et al, Ana;. Bioanal. Chem., 2011, 400:2763-2773. published online: Mar. 20, 2011 (Year: 2011).*

A.I.M. Athamneh et al: "Phenotypic Profiling of Antibiotic Response Signatures in *Escherichia coli* Using Raman Spectroscopy"; Antimicrobial Agents and Chemotherapy, vol. 58, No. 3, Dec. 2, 2013, pp. 1302-1314.

Assmann Cora et al.: "Identification of vancomycin interaction with Enterococcus faecaliswithin 30 min of interaction time using Raman spectroscopy"; Analytical and Bioanalytical Chemistry, Springer, DE, vol. 407, No. 27, Aug. 1, 2015, pp. 8343-8352.

E. Consuelo Lopez-Diex et al: "Monitoring the Mode of Action of Antibiotics Using Raman Spectroscopy: Investigating Subinhibitory Effects of Amikacin on Pseudomonas a eruginosa"; Analytical Chemistry, vol. 77, No. 9, May 1, 2005, pp. 2901-2906.

Gyeong Bok Jung et al.: "Evaluation of antibiotic effects on Pseudomonas aeruginosa biofilm using Raman spectroscopy and multivariate analysis"; Biomedical optics Express, vol. 5, No. 9, Aug. 28, 2014, p. 3238.

International Search Report for Application No. PCT/FR2016/053100.

Kai Zhao et al: "Fabrication of silver-decorated sulfonated polystyrene microspheres for surface-enhanced Raman scattering and antibacterial applications", vol. 5, No. 85, Aug. 10, 2015, pp. 69543-69554.

Paul R. Carey et al.; "New Techniques in antibiotic discovery and resistance: Raman spectroscopy"; Annals of the New York Academy of Science, vol. 1354, Aug. 14, 2015, pp. 67-81.

Ting-Ting Liu et al: "A High Speed Detection Platform Based on Surface-Enhanced Raman Scattering for Monitoring Antibiotic-Induced Chemical Changes in Bacteria Cell Wall"; col. 4, No. , May 7, 2009, pp. e5470-e5470.

Ute Munchberg e al: "Raman spectroscopic identification of single bacterial cells under antibiotic influence"; Analytical and Bioanalytical Chemistry, vol. 406, No. 13, Mar. 21, 2014, pp. 3041-3050.

* cited by examiner

FIGURE 3
| $C_0$ | $C_1$ |
|---|---|
| $C_2$ | $C_3$ |
| $C_4$ | $C_5$ |
FIGURE 4
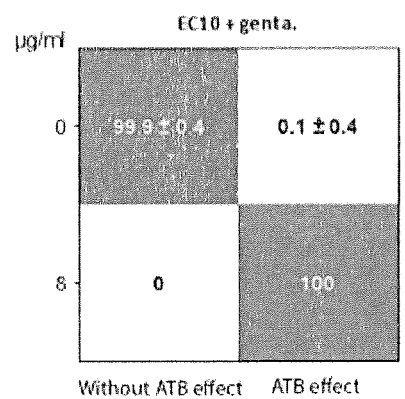
FIGURE 5
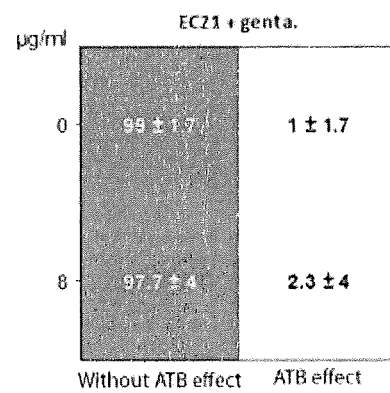

METHOD FOR DETERMINING THE REACTION OF A MICROORGANISM TO ITS EXPOSURE TO A CHEMICAL COMPOUND

CROSS REFERENCE TO RELATED APPLICATIONS

This application is a National Stage of PCT Application No. PCT/FR2016/053100 filed on Nov. 25, 2016, which claims priority to French Patent Application No. 15/61446 filed on Nov. 27, 2015, the contents each of which are incorporated herein by reference thereto.

TECHNICAL FIELD

The invention falls within the scope of the analysis of the sensitivity phenotype of microorganisms to antibiotics. It concerns the determination of the reaction of at least one microorganism of interest to its exposure to an antibiotic implementing a Raman spectroscopy analysis and its applications.

BACKGROUND

The term "microorganism" covers any microorganism that could react to its exposure to an antibiotic, such as bacteria or yeasts. Although the invention is more specifically described hereinafter with reference to bacteria, it is meant that it is not restricted thereto.

This determination is of major interest in the microbiological diagnosis in the fields of health, agri-food, environment, it can be just as important in pharmacology, in the screening of new molecules, in particular antibiotics, or in the search for cytotoxic compounds present in food products, for example milk. This selection of applications is not exhaustive, and in general, the invention can find application in any field the moment the question was raised of the reaction of cells to an exposure to a chemical or biological compound.

The Raman effect is a light diffusion phenomenon that applies to the vast majority of molecules. Its observation in spectroscopy allows characterizing a molecule, a microorganism, a medium, it is of a simple implementation, it is fast and cost-effective, and has the substantial advantage in biology of not being strongly disrupted by water and of not requiring a labelling or a contrast agent.

Thereby, according to the document AIM Athamneh et al. (2014) Antimicrob Agents Chemother 58:1302-1314, the authors used Raman spectroscopy in order to characterize the sensitivity of *E. coli* cultures to 15 known antibiotics representing 5 families of antibiotics, in order to constitute a baseline. For this purpose, the described method comprises the following steps, producing an *E. coli* culture, exposing a sample of this culture to antibiotics in a concentration of triple the minimum inhibitory concentration (MIC), maintaining said cells in contact with the antibiotic for at least 30 minutes, harvesting and washing bacterial cells, collecting a cell suspension and treating for analyzing the cell layers by Raman spectroscopy. The result of the analysis is derived from the average of a multiplicity of spectra obtained for each collection comprising a multitude of cells and integrated into the reference base. Once constituted, this reference base can be exploited in order to allocate an unknown antibiotic to one of said 5 families, depending on the sensitivity of an *E. coli* culture to that antibiotic. The classification performances obtained accordingly allow obtaining elements as to the class of the unknown molecule, which can be useful for pharmacological research. The obtained results, however, do not provide information related to the sensitivity phenotype of the studied bacteria or information that is conducive to clinical use.

The document WO2013/093913A1 describes a method for identifying a bacterium in a biological fluid using in particular Raman spectroscopy. A sample of a bacterial culture of said biological fluid is submitted to an incident light and the resultant light obtained by diffusion is analyzed by Raman spectroscopy. The read signal is then interpreted thanks to a reference base listing the spectral signature of different microorganisms defined in the same conditions. This method may further comprise a step of exposing said bacteria to an antibiotic, the read signal being an effect of said antibiotic on those bacteria. The measured effect of the antibiotic is exerted in particular on the viability of the bacterial cells or on the development of the culture. The disadvantage of this method lies in its use of a culture step which not only protracts the acquisition of an answer, but also, moreover, requires mastering an additional step necessary for obtaining the expected answer.

If using Raman spectroscopy allows lightening the determination of the sensitivity clinical profile of bacteria of interest to an antibiotic, the fact remains that, according to this prior art, it is applied to a bacterial culture whose obtaining within a time of about 18 to 24 hours, does not allow accessing a rapid determination method. In diagnosis, this constitutes a major obstacle to an effective care of patients.

According to the document U. Münchberg et al. (2014) Anal Bioanal Chem 406: 3041-3050, the authors raise the problem of the rapid establishment of an appropriate antibiotic treatment in a patient, as well as the difficulties encountered by techniques using a cell culture when the patient has already received an antibiotic treatment. The authors then dispense with the culture step and apply Raman spectroscopy to individual bacteria. This work therefore addresses the issue of identifying bacteria previously exposed to an antibiotic, a potential source of misdiagnosis. In order to solve this problem, the authors constitute a reference base comprising the results of Raman analysis performed on individual cells which were not exposed to an antibiotic and on cells which were exposed to an antibiotic, in various concentrations lower than the minimal inhibitory concentration (MIC). The conclusion of this study is an absence of major difficulty in identifying the bacteria under these conditions. The authors did not notice any significant effect of the antibiotics on the bacterial spectra and conclude that the possible modifications are observed in areas of high variability and therefore unusable.

None of these solutions allows considering a reliable method for determining the sensitivity clinical profile of a bacterium of interest to an antibiotic and in particular determining its resistance or sensitivity to an antibiotic, in a short time in the range of a few hours which would allow having a diagnosis within the day. This lack is responsible for ineffective antibiotic therapy, for risk of worsening the infection of the patient and for a difficulty in establishing an accurate diagnosis when the patient has already been treated. This lack is all the more felt at the time of emergence and spread of multi-antibiotic resistant bacteria.

BRIEF SUMMARY

The invention provides an answer to this need with a method for determining the reaction of a bacterial strain of interest to its exposure to an antibiotic, requiring no culture, whose result which is accessible in about 2 hours is therefore very fast compared to the state-of-the-art methods (36 h-72 h), and furthermore reliable.

The invention concerns a method for determining the reaction of at least one microorganism of interest, such as a bacterium of interest, to its exposure to an antibiotic implementing a Raman spectroscopy analysis and comprising the following steps:

Having a biological sample that could contain said bacteria of interest,

Preparing at least two fractions of said sample each comprising one or more living bacterium/bacteria of interest, Capturing, in each fraction, at least one living bacterium of interest by using a binding partner, Exposing at least one of the fractions to at least one concentration of at least one given antibiotic, the other of the fractions being the control fraction, Submitting the bacterium/bacteria of interest contained in the fractions to an incident light and analyzing the resultant light obtained by Raman diffusion by the bacterium/bacteria of interest by Raman spectroscopy in order to obtain as many Raman spectra as bacteria, Submitting the material constituting the support in the fractions to an incident light and analyzing the resultant light obtained by Raman diffusion of said support by Raman spectroscopy in order to obtain some Raman spectra of this support, Treating said spectra in order to obtain a signature of the reaction of the or each bacterium of interest to the exposure of said antibiotic and of the control, Comparing the signature obtained accordingly per bacterium of interest to a reference base defined under the same conditions as above for different bacteria and at least said antibiotic, and Defining a sensitivity clinical profile of said bacterium of interest to said antibiotic.

The advantage of the method of the invention compared to the aforementioned state of the art is that it allows obtaining a relevant signal correlated with the chemical modifications of the microorganisms in response to their exposure to the tested compound using Raman spectrometry, for individual cells. Not only does it dispense with the cell culture step, but it also provides information per analyzed cell. Unlike known methods, the information is not obtained by calculating an average of the analysis results or by obtaining a physically averaged measurement. It is the expression of a result per cell, which leads to a more relevant information in that it allows detecting a variability, which could be substantially different from that resulting from an average of results that conceals any heterogeneity. Of course, according to the considered applications, the information can be obtained from the result of several individual cells.

According to the invention, a method for determining the reaction of a bacterium to its exposure to an antibiotic by Raman spectroscopy is provided, which is suitable for all the applications considered above. It can actually be intended for characterizing the sensitivity clinical profile of a bacterium of interest to an antibiotic, in a biological sample, but it can also be arranged for the screening of antibiotic molecules. Since it does not use a culture step, it is also suitable for the analysis of non-culturable cells.

Before going in more detail into the description of the method of the invention, some used terms are defined hereinafter.

"Biological sample" means a tissue, a fluid, as well as components of said tissue and fluid. According to the field of application of the method, and by way of non-restrictive examples, the sample may be of human or animal origin such as blood, urine, saliva, breast milk; it can be of plant origin, a food extract, an extract of the soil . . . .

"Reaction of a microorganism of interest such as a bacterium of interest to its exposure to an antibiotic (ATB)" means any modification, for example metabolic modification, which can be detected by Raman spectroscopy in regard to the same bacterium not exposed to an antibiotic.

The minimum inhibitory concentration (MIC) of an antibiotic for a given bacterium, expressed in µg/ml, is the lowest concentration of said antibiotic of a range of dilutions capable of stopping bacterial growth.

A clinical breakpoint is a given concentration of an antibiotic defined for a species, determined by the EUCAST (European Committee for Antimicrobial Susceptibility Testing) on the basis of microbiological criteria and pharmacokinetic and pharmacodynamic data. Conventionally, two different breakpoints, called threshold values, are defined and thus determine an interval of concentrations. When the MIC of a tested strain is below this interval, the tested strain is described as sensitive, that is to say it is capable of being inhibited in vivo therefore implying a high probability of therapeutic success; if it is in this interval, the bacterium is called intermediate bacterium, and if it is beyond this interval, the bacterium is called resistant bacterium, that is to say, it withstands antibiotic concentrations higher than those acceptable in vivo and for which there is a high probability of therapeutic failure.

"Signature of the reaction of a microorganism of interest to its exposure to a chemical compound" means any variation, for example metabolic or constitutional variation, expressed by said microorganism specifically in response to its contact with said compound and which can be detected by Raman spectrometry. In order to more easily highlight these variations, the result of one or more step(s) of treating the Raman data resulting in a signal used to perform the test can also be called a signature. For example, we can choose to subtract an initial state or a condition where the bacteria of interest have not been exposed to the compound tested to the spectra acquired on exposed bacteria.

Preferred variants of a method of the invention are hereinafter exhibited, they must be considered alone or in combination. They are more suitable for diagnostic applications, and precisely for determining the sensitivity clinical profile of a bacterium to an antibiotic in a biological sample, but as mentioned previously, the method of the invention is not restricted to such applications.

Determining the sensitivity clinical profile of a bacterium to an antibiotic consists first of all in identifying the sensitivity phenotype of a bacterium to an antibiotic. Thus, more than two fractions of said sample are preferably prepared and at least two fractions are exposed respectively to increasing concentrations of the antibiotic. According to variants of the method of the invention, at least three fractions of said sample, or even four or five or more, are exposed respectively to increasing concentrations of the antibiotic.

Advantageously, the concentrations of said antibiotic are selected within an interval of values reflecting conventional concentrations of in vitro tests, thus allowing a comparison to the current reference data, for example to microdilution tests. According to a preferred variant, the concentrations of the antibiotic to which the fraction(s) is/are respectively exposed, are comprised within an interval of values including at least one of the values selected from the typical MICs and the threshold values of clinical breakpoints for the pair species/tested antibiotic, or concentration panels used in reference methods. In a diagnostic application of the method of the invention, these concentrations are therefore specifically selected according to the considered bacterium/antibiotic pair. For example, for the pair *E. coli*/Gentamicin for which the typical MIC, or the epidemiological cut-off of the species, is 2 µg/mL and the two clinical breakpoints are 2 and 4 µg/mL, they can be comprised within an interval of values including at least one of the values selected from 1, 2, 4 and 8 and 16 µg/ml, preferably two or even three or four of these values or even these five values.

The method of the invention comprises a step of capturing a bacterium of interest by means of a binding partner. A binding partner according to the invention recognizes specifically or not specifically a bacterium of interest for the capture thereof in order to analyze it. During its interaction with the bacterium, the binding partner may be present in the free state in the medium or may have been previously immobilized on a support. If the adhesion of the bacteria on the binding partner takes place in the medium, an immobilization of said partner on the support can be performed next. "Immobilization on a support" means direct or indirect immobilization of said binding partner on said support, by any means well known to those skilled in the art. A binding partner according to the invention may be of a biological and/or chemical nature. Thus, for example, in case of nonspecific or generic capture of cells, it may consist in a chemical compound or carry chemical functions which will interact with the cells. Polymers of the chitosan, poly-L-lysine, polyethyleneimine and polyaniline type are illustrative. It may consist in a biological molecule such as selected from proteins, antibodies, antigens, aptamers, phages, phage proteins; this will be generally a specific capture of the cells. In an advantageous variant of the invention, the binding partner is immobilized on the support and then on the bacterium captured by said immobilized binding partner.

The capture step may be performed on fractions of one or more bacterium/bacteria exposed to an antibiotic and on the control fraction, after concentration of said fractions. For example, said fractions are concentrated by centrifugation and then the pellets that are subjected to the capture step are retrieved. Advantageously, the capture is directly carried out in the biological sample without a separate pellet concentration step.

After the capture step, the captured bacteria are marked and sorted. This step is carried out for example by imaging or spectrophotometry. Non-captured bacteria can then be eliminated.

The preferred conditions of exposure of the bacteria to the antibiotic are mentioned hereinafter:

The antibiotic is in a physiological medium allowing at least to keep the bacterium/bacteria of interest alive.

The exposure to the antibiotic is carried out at a culture temperature of the considered strains of about 18° C. to about 40° C., typically between 28° C. and 37° C. for strains of clinical interest.

The exposure to the antibiotic is carried out for a time called incubation time much shorter than the time required in the reference methods. According to the invention, the incubation time is advantageously of at least 10 minutes and at most of 4 hours.

The acquisition of a signature for each fraction exposed to the antibiotic will be illustrated in the examples.

In general, several methods can be used for treating the obtained data in order to achieve the result. In order for it to be as relevant as possible, a complete method for treating the spectra at individual level is preferably performed. It is divided into two major steps, a pretreatment step consisting in treating the spectra for maximizing the extraction of a signal of interest and a classification step allowing to perform the actual test of interest and achieve the result of interest.

The pretreatment step comprises at least one, preferably two, and more preferably all of the operations mentioned below:

Removal of the saturated spectra

The removal of the saturated spectra is the first step of pretreating the spectra. It is carried out from the obtained raw spectra. The spectra for which more than 20% of the channels of the region of interest have an intensity greater than 99% of the maximum intensity are considered to be saturated.

Removal of the cosmic rays

The rays called "cosmic" rays are particles charged with high energy, of solar, galactic or extragalactic origin, that constantly bombard the CCD detector (Charge-Coupled Device, charge transfer device). They cause very sharp signal peaks that can appear randomly in the spectra. A search for peaks is first performed from the calculation of the second derivative of the raw spectrum. A comparison of this second derivative and of the second derivative of the smoothed raw spectrum allows then identifying the very sharp peaks for which the smoothing has significantly decreased the height of the peak, that is to say the cosmic rays. The peaks associated to cosmic rays are replaced by a traight line.

Realignment

Slight offsets have been noticed between series of spectra taken at different dates. This offset is a constant across the entire spectrum. It is preferable to correct it.

The method consists in realigning all the spectra with respect to a "reference" constituted by the positions of 2 peaks 1001 $cm^{-1}$ and 1126 $cm^{-1}$. The position of the peaks of the spectra to be realigned is determined from an adjustment of the peaks by a model composed of a Gaussian on an affine background.

Spectra on individual bacteria generally do not allow making a realignment by spectrum (too noisy spectra). The realignment is therefore preferably made from the average spectra of the bacteria (after removal of the background by SNIP algorithm). A comparison between the position of 2 peaks in the average net spectrum to be realigned and the reference values of these same 2 peaks allows measuring the offset. The correction found from the spectra of the bacteria is applied to the environmental spectra of the same date acquired on the material constituting the support.

Extraction of the specific bacterial signal

The subtraction of the background is made in two steps. A first background, constituted of an average spectrum of the material constituting the support, is adjusted for example between 450 and 650 $cm^{-1}$ to the bacterium spectrum in the case of a glass support because it is a region where there is only but the spectral contribution of glass. This adjustment is made with the constraint of staying below the bacterium spectrum in this region. The second step consists in subtracting a background by the SNIP algorithm.

Removal of the deviants

An automatic removal module for deviant spectra has been developed. The spectra used in the search for deviants are the normalized net spectra used in the subsequent analysis. The search for deviants is applied to a group of spectra corresponding to a strain, a given antibiotic concentration and a given date. The method is based on calculating the Euclidean distance between each spectrum and the average spectrum of a group of spectra. This removal of the deviants is performed twice consecutively. The first round allows removing very aberrant spectra which have a significant effect on the average spectrum.

Region of interest and normalization of the signal

The choice of the region of interest is important because it is on this region that the spectra will be compared with each other. The spectra are measured between 400 and 3080 cm$^{-1}$ of energy offset. The retained region of interest is [650-1750] cm$^{-1}$ and/or [2800-3050] cm$^{-1}$. It is essential to normalize the net signals so that they can be compared directly with each other. The used normalization interval is [650-1750] cm$^{-1}$ or [2800-3050] cm$^{-1}$. The net signal is divided by the value of the average of the net signal in this interval. It is useful, in an advantageous embodiment, to subtract a reference state of the bacteria from all the acquired spectra of individual bacteria. The used reference state is the one constituted of spectra from $S_0$. This operation allows overcoming the variations in growth conditions, the variations of the interface I (see FIG. 2) and extracting a signal called signature related to the exposure to variable antibiotic agent concentrations.

As indicated above, the method has a strong interest in its application for determining the clinical phenotypic profile of a bacterium of interest and in particular for determining its sensitivity or its resistance to an antibiotic, and advantageously determining the MIC of said bacterium to said antibiotic.

In this indication and to obtain a relevant result, it will be preferred that each fraction comprises at least 2, preferably at least 5, bacteria of interest in order to obtain at least 2, preferably at least 5 signals.

According to a variant of the invention, the compared bacteria are substantially at the same stage of growth.

In general, a method of the invention can be implemented in a system including the following elements:

A spectrometer allowing the Raman analysis of the sample:

The used Raman spectrometer is conventionally called a confocal Raman micro-spectrometer in the state of the art in that it is constituted of an analysis stage capable of producing a spectrum from the light resulting from the Raman diffusion after excitation by a laser, the Raman spectrometer, this analysis stage being coupled to a confocal microscopy stage allowing to measure a Raman spectrum using a microscope lens and to limit the analyzed volume to a spatially restricted volume, the confocal volume. The microscopy stage of the micro-spectrometer can also allow conventionally acquiring images by a camera present in the device or more simply by direct observation via eyepieces using a light source integrated or not to the micro-spectrometer;

A device for conditioning micro-organisms for spectral analysis; and

A computer allowing to drive the micro-spectrometer, the storage of collected data and the analysis of these data using a dedicated software implementing the methods below.

A device for conditioning microorganisms as mentioned above, optionally coupled to a spectrometer and to a computer for implementing the method of the invention is also an object of the invention.

A system as discussed above, allowing to implement a method of the invention is illustrated in FIG. 1 and its putting into practice is carried out in the following examples. They are described in more detail hereinafter:

The system comprises a Raman micro-spectrometer allowing the confocal analysis of the light diffused by objects of the size of the microorganisms (0.5-100 µm), for example an ARAMIS spectrometer of the brand HORIBA equipped with a ZEISS microscope lens of the 100× PLAN-NEOFLUAR type of the reference 44 080. This microspectrometer is equipped with manual (eyepieces) or digital (CCD camera, for example of the brand IDS model µEYE UI-1240ML) viewing means allowing to observe samples in measurement position. The Raman measurement parameters are selected appropriately for the studied object. In the following examples, the confocal volume has been adapted to be close to the size of a bacterium (typically a 300 µm confocal hole on the used ARAMIS model) in order to limit the non-searched spectral contributions.

The system also comprises a conditioning device, which is an object of the invention, of which a preferred embodiment D is illustrated in FIG. 2. This device includes: a part P comprising recesses corresponding to a set of chambers (from $C_1$ to $C_N$), N being equal to at least 2, said chambers being optionally fluidly isolatable, an optional set of ports $P_1$ to $P_{2N}$ allowing the connection of the fluidic chambers to a liquid management system, a functionalized or non-functionalized optical interface I compatible with the spectral measurement on microorganisms; and an optional portion J ensuring the assembly between the parts I and P.

According to a simplified variant of a conditioning device of the invention, it can be a standard microscope slide I (25 mm×75 mm×1 mm, for example of the reference 631-1551 from VWR) constituting the part P, two double-sided adhesives serving as fluidic chamber (for example of the reference AB-0577 from THERMO SCIENTIFIC commonly called "Gene Frame") constituting the seal J and a coverslip (for example of the reference 0107052 from Marienfeld) constituting the interface I.

The interface I can be functionalized by a capture chemistry called "generic" capture chemistry that will be based on properties generally encountered in microorganisms in solution or by a capture chemistry called "specific" capture chemistry and based on particular properties of a searched species. For example, the "generic" capture chemistry can be materialized by absorbing on the coverslip polycationic molecules (such as polyethylenimine, poly-L-lysine or chitosan . . . ) and the specific capture chemistry can be materialized by adsorbing or coupling biological molecules such as proteins, antibodies, antigens, aptamers, phages or phage proteins to the glass surface in order to allow capturing a microorganism of interest.

The conditioning device ensures the physicochemical conditions (temperatures, gas . . . ) enabling the microorganisms of interest to have a metabolic activity.

Variants of this device D are of course possible and fall within the scope of the present invention.

In a preferred implementation, the following steps are performed:

introducing a solution containing the microorganisms of interest in the chambers $C_1$ to $C_N$, using the respective fluidic connection ports $P_1$ to $P_N$, respecting a time called latency time to cause the microorganisms of interest to adhere to the surface I by interaction with the functionalization, introducing, respectively, an increasing series of concentrations of the tested chemical compound ($C_2$ to $C_N$) in liquid solution and a predetermined amount of physiological medium in each fluidic chamber $C_1$ to $C_N$, observing a time called incubation time during which the microorganisms of each chamber are exposed to the chemical compound, excepting those of the chamber $C_1$ (control), ensuring the marking and the sorting of the microorganisms captured on the surface I, performing Raman spectral measurements on the microorganisms isolated in the previous step until obtaining a set of spectra $S_1$ to $S_N$ constituted of the acquired spectra for the microorganisms of each of the fluidic chambers $C_1$ to $C_N$, then performing a direct analysis of the acquired spectra by comparing the evolution of the spectra from $C_1$ to $C_N$ with a previously constituted database, or by searching for a spectral signature by determining the set of spectra $S_i$ having a significant evolution, the result of the analysis is constituted by the concentration $C_i$, the comparison of $C_i$ with a reference threshold or the expression of the evolution of some features of the spectra $S_i$ according to the concentration; it allows describing the phenotypic behavior of the analyzed microorganisms relative to the tested compound.

As indicated above and according to the desired objective for the measurement, several adaptations can be made (number of tested concentrations, incubation time . . . ), the general principle remaining identical.

BRIEF DESCRIPTION OF THE DRAWINGS

The details and advantages of the invention will emerge from the examples hereinafter, in support to the following figures according to which:

FIG. 3 illustrates placing the samples on a glass slide of the conditioning device illustrated in FIG. 2.

FIG. 4 represents an expression of the reaction of the *Escherichia coli* strain of the reference ATCC 25922, called "EC10", to gentamicin, obtained according to the method of the invention.

FIG. 5 represents an expression of the reaction of the *Escherichia coli* strain of the reference ATCC 35421, called "EC21", to gentamicin, obtained according to the method of the invention, for N=5.

DETAILED DESCRIPTION

Figure 1:
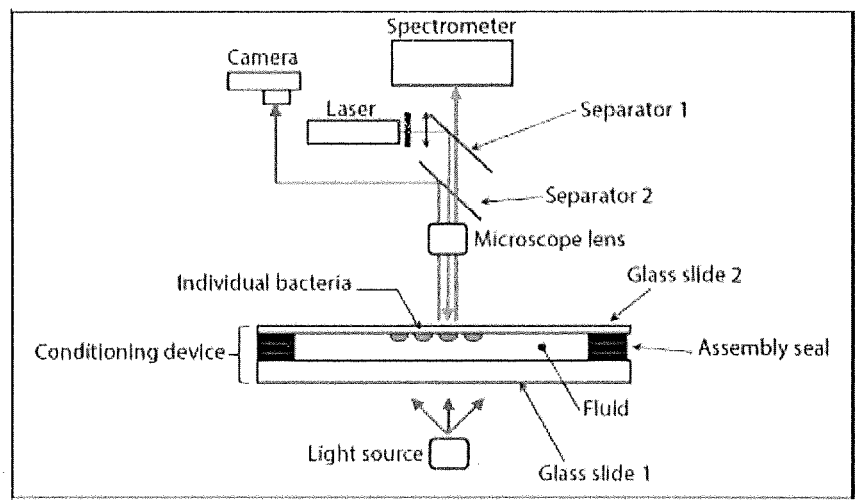
FIG. 1 shows the block diagram of the complete mounting of a system allowing to implement the method of the invention integrating a device of the invention as illustrated in FIG. 2.
Figure 2:
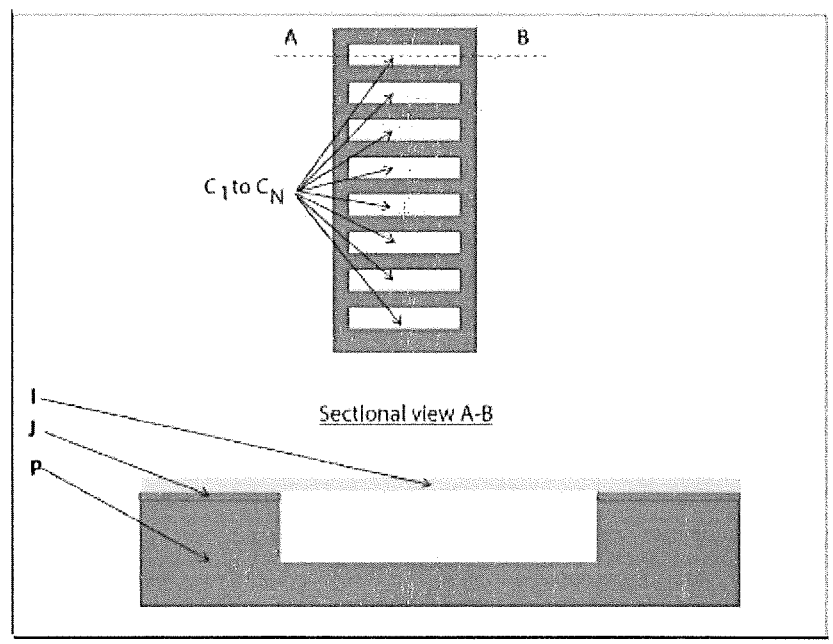
FIG. 2 represents the block diagram of the device for conditioning microorganisms belonging to the system illustrated in FIG. 1.

Example 1: Application of the Method of the Invention for Determining the Sensitivity Phenotype of the *Escherichia coli* Strain of the Reference ATCC 25922 Called "EC10" to Gentamicin The retained conditioning device is constituted of two fluidic chambers and two antibiotic concentrations are tested: $c_0$: "Without antibiotic" and "Resistance test".

Let $c_1$ be the concentration of gentamicin: $c_1=8$ μg/mL, which corresponds to the doubling of the concentration 4 μg/mL corresponding to the clinical breakpoint as defined by the EUCAST. The objective of this test is to determine whether the bacterium is considered as resistant according to the definitions provided by the EUCAST.

A solution containing the bacteria to be tested is used as a test sample. This solution is obtained by suspending $5.10^7$ CFU/mL in order to have a concentration potentially encountered in a clinical sample, for example a urine collection. This bacteria solution is brought into contact with the interface I of the device functionalized by adsorbing polyethylenimine (PEI) (generic capture). After a capture time of 10 minutes allowing the bacteria to come into contact with the functionalization, the interface I is washed with a water solution, this optional step allowing to eliminate the surplus of uncaptured bacteria still in solution. The physiological medium retained in this example is constituted of a poorly enriched mixture of Bouillon TSB-T Trypcase Soy broth (for example of the reference 42100 of bioMérieux) and of PBS 10× (for example obtained from the PBS tablets of the reference A9162, 0100 of the brand AppliChem) in a 1:9 ratio. After dividing this physiological medium into two fractions, an amount of gentamicin (for example of the reference G1397-10ML of Sigma-Aldrich) is added respectively to each of these fractions, allowing to obtain a different concentration of gentamicin $c_0$ or $c_1$. The solutions of concentrations $c_0$ and $c_1$ produced accordingly are respectively introduced into the chambers $C_0$ or $C_1$. The bacteria captured directly from the sample on the surface I are thus exposed, in a suitable medium, to a different antibiotic concentration depending on the chamber in which they are present.

The device is then heated in order to reach a temperature of 37° C. for two hours and then placed in measurement position on the micro-spectrometer. The marking of the captured bacteria is carried out by an automatic procedure based on image analysis, by a conventional procedure for detecting particles, acquired by means of the micro-spectrometer camera and a suitable light source. This marking allows acquiring automatically a series of Raman spectra ($S_0$ and $S_1$, respectively) acquired on individual bacteria present in each chamber $C_0$ and $C_1$. The number of spectra to be acquired for constituting a dataset depends on the level of requirement on the performances of the tests to be carried out.

As mentioned previously, several methods can be used for treating the data obtained in order to achieve the result. In the present example, a complete method for treating spectra individually comprising a pretreatment step comprising all the phases described above is used in order to maximize the extraction of a signal of interest and the classification.

In this example, a set of at least 2N spectra extracted from the total set M of the acquired spectra is used: N spectra from $S_0$ and N spectra from $S_1$. These spectra are drawn without replacement among the available M spectra. The average of N spectra from $S_0$ is subtracted from each of the N spectra from $S_1$ and the N spectra from $S_0$, these two batches of spectra constituting a "control test sample" and a "resistance test sample".

For the classification, a reference database is used in the present example, obtained from similar experiments carried out previously at dates and from different cultures in order to train a classifier obtained using a Support Vector Machine (SVM) with radial kernel. This classifier is trained to recognize two classes, one "Without antibiotic effect" from spectra from conditions without antibiotic and the other "Antibiotic effect" from spectra previously acquired under conditions where the concentration is higher than the MIC of the strain(s) used in the reference base. For each test sample constituted of N difference spectra, these difference spectra are tested individually with respect to the classifier and the majority class among the elements of the groups is assigned to the group of N spectra. This majority assignment is based on the good correlation of the results obtained accordingly with the reference methods but can well be modified in order to take into account some other parameters of the tests. For example, a vote to a threshold different from the majority where, as soon as the number of bacteria having no effect exceeds 30%, then a result "Without antibiotic effect" is conservatively assigned. This threshold may also be adjusted in order to take into account the incubation time: thus for example, if the time of exposure to antibiotics is significantly reduced, or if the tested microorganism has a slower typical doubling time, it is necessary to take into account a lower threshold in order to assign an "Antibiotic effect" result to this group of spectra. Finally, a more nuanced system where each bacterium is considered in a completely individual way could be adopted. This last embodiment may be advantageous if the method of the present invention is used for research purposes.

In order to illustrate the performances obtained accordingly, the average score obtained for all the results that would be obtained with a combination of 5 spectra per concentration (N=5) out of a total set of total acquired spectra of 294 spectra (M=294) is shown in FIG. 4. This matrix has, in columns, the states "Without ATB effect" and "ATB effect" and, in rows, the two concentrations of tested antibiotics. The score indicates the percentage of the test samples that are assigned to a given class by the classifier described above. Thus, it is found that 99% of the samples of N=5 bacteria of the "control test sample" are classified as "Without antibiotic effect" and 97.1% of the "Sensitivity test samples" constituted of bacteria exposed to the test concentration are classified as "ATB effect". The strain can therefore be described as sensitive according to the invention with a high reliability on the basis of only a few individual bacteria analyses. The result is consistent with the reference methods [BioMérieux products ETEST® (antimicrobial susceptibility testing kit) GM 256 (ref. 412368) and VITEK® card N233 (Gram Negative Susceptibility card; ref. 413117)] which give as a result a MIC=1 µg/mL, which confirms that the bacterium is not resistant according to the EUCAST, its MIC not being strictly above the threshold defined by this organism.

Example 2: Application of the Method of the Invention for Determining the Sensitivity Phenotype of the *Escherichia coli* Strain of the Reference ATCC 35421 Called "EC21" to Gentamicin A test identical to that of Example 1 is conducted on another strain of *Escherichia coli*, the strain ATCC 35421 called "EC21" allows confirming the discriminatory nature of the measurement.

The results are shown in FIG. 5.

The reference methods assign a MIC>256 µg/mL to this strain which is therefore resistant according to the EUCAST.

The method of the invention confirms this result since in the case where N=5 and M=133, it can be read that 100% of the performed tests do not show a characteristic effect profile of the antibiotic agent.

Example 3: Determination of the Minimum Inhibitory Concentration (MIC) of Two Strains of *Escherichia Coli* to Amoxicillin In this example, the aim is to determine the sensitivity phenotype, and to specify a framework of the minimum inhibitory concentration of the *Escherichia coli* strain of the reference ATCC 25922 called "EC10" for an antibiotic, amoxicillin, having a mode of action different from that provided in Examples 1 and 2.

In order to illustrate the discriminating power of this method, the same test performed for a strain of *Escherichia coli* ATCC 35421 resistant to amoxicillin called "EC21" is also shown.

The following concentrations of amoxicillin have been tested.

EC10 sensitive strain ($MIC_{REF}$=6 µg/mL):
0 µg/mL; 2 µg/mL; 4 µg/mL; 8 µg/mL and 16 µg/mL
EC21 resistant strain ($MIC_{REF}$=256 µg/mL):
0 µg/mL; 4 µg/mL and 8 µg/mL.

In this example, another embodiment of the provided test corresponding to the described alternative method is illustrated.

A solution containing the bacteria to be tested, EC10 or EC21, is used as test sample. This solution is obtained by suspending 5 $10^7$ CFU/mL in water in order to have a concentration potentially encountered in a clinical sample, for example a urine collection. This bacteria solution is distributed in 5 filter tubes (for example MICROCON (Centrifugal filters) YM100 from Millipore) at a rate of 150 µL per tube. A sufficient amount is added to each of these tubes for the final 250 µL of physiological medium allowing the growth constituted in this example of a mixture of PBS of final concentration of 1× (obtained from the PBS tablets of the reference A9162,0100 of the brand AppliChem), of a nutrient medium TSB 0.1× (for example obtained from Bouillon TSB-T Trypcase Soy broth of the reference 42100 of bioMérieux) and of an amount of amoxicillin allowing to achieve respective final concentrations $c_0$ to $c_4$ of amoxicillin (for example the reference A8523-10ML of Sigma-Aldrich) as follows:

$c_0$=0 µg/mL
$c_1$=2 µg/mL
$c_2$=4 µg/mL
$c_3$=8 µg/mL
$c_4$=16 µg/mL

The 5 tubes obtained accordingly are incubated for 2 hours at 37° C. with stirring. Centrifugation at 1200 g for 8 minutes using a centrifuge adapted to the used containers (for example the model 8415C of the brand Eppendorf) then allows retrieving a bacterial pellet on the filter portion of each tube and eliminating the medium. The bacterial pellets are respectively resuspended in water in order to carry out a washing before being again pelletized by centrifugation (1200 g for 10 minutes) always on the filter portion of the tube. These pellets are distributed on a glass slide of the Marienfield type constituting the interface I (not functionalized in this configuration) by means of a swab in corresponding chambers noted $C_0$ to $C_4$. In this configuration, the chambers are not necessarily isolated from a physical point of view since no exchange is possible between the different conditions. It is thus possible to use a glass slide whose virtual compartments are clearly identified for each concentration as shown in FIG. 3. The virtual compartments are defined by delimitations materialized in the present example by a labelling previously made on the slide on the opposite side to that where the bacteria are deposited. The glass slide is then deposited on a "geneframe" constituting the seal J in the conditioning device described above.

The marking of the captured bacteria is performed by a manual procedure in this example based on the visual analysis by the operator of the image acquired by means of the camera of the micro-spectrometer and a light source adapted by an experimenter. This marking allows acquiring a series of at least N Raman spectra acquired on individual bacteria present respectively in each chamber $C_0$ to $C_4$. The number of spectra to acquire for constituting a dataset depends on the level of requirement on the performances of tests to be carried out.

Figure 6:
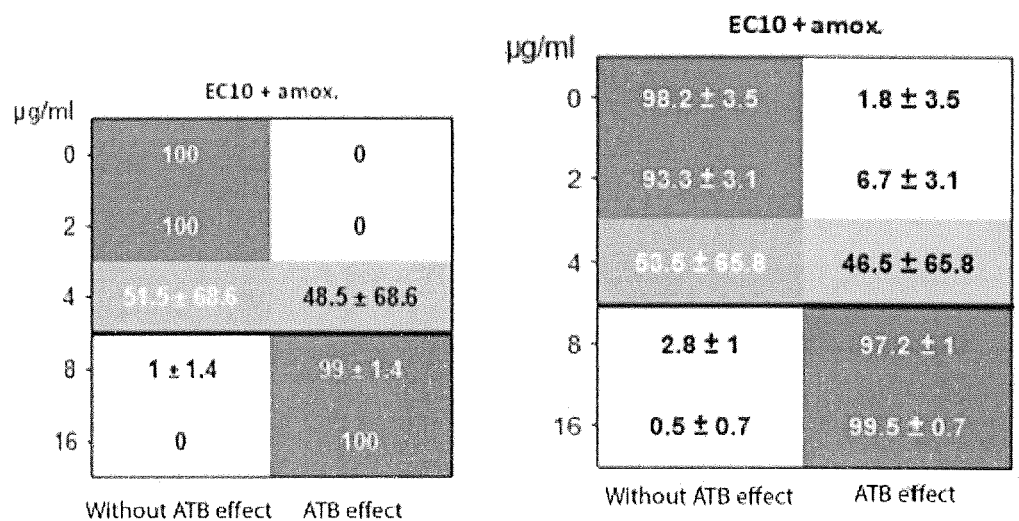
FIG. 6 represents the confusion matrix obtained for the sensitive strain of *Escherichia coli* of the reference ATCC 25922, called "EC10", in the presence of amoxicillin (MIC=6 μg/mL) for N=11.

The data treatment mode proposed here is identical to that of Examples 1 and 2: a first pretreatment step followed by a step of classifying the acquired spectra using a previously trained classifier. In the examples provided below, the classifier is trained with a reference base containing "Without antibiotic effect" spectra previously acquired in a condition without amoxicillin antibiotic (0 µg/mL) of EC10 bacteria and "Antibiotic effect" spectra of EC10 bacteria in the presence of 8 µg/mL of amoxicillin. The results obtained are shown in the confusion matrix provided in FIG. 6. As previously, this matrix allows demonstrating the robustness of the method by giving the results for a large number of tests.

A transition in the assignment of the spectra groups of the "Without ATB effect" category to the "Antibiotic effect" category is observed between the concentrations of 4 µg/mL and 8 µg/mL. A MIC comprised between 4 µg/mL and 8 µg/mL can therefore be assigned to this strain according to the assays. This variability to a dilution factor is very frequent in this type of assay, the EUCAST indicates, for example, ranges of MIC variations of [2-8]µg/mL for this strain ATCC 25922 during quality controls of the MIC disc diffusion tests, and is therefore consistent with expected results. The result established by the reference methods [BioMérieux products ETEST® (antimicrobial susceptibility testing kit) AM 256 (ref. 412253) and VITEK® card N233 (Gram Negative Susceptibility card; ref. 413117)] is 6 µg/mL for this strain, which is also consistent with this result.

Figure 7:
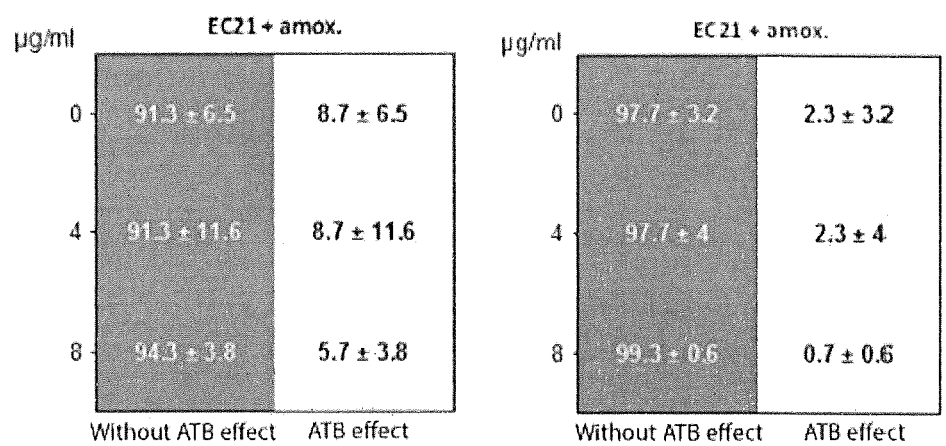
FIG. 7 represents the confusion matrix obtained for the sensitive strain of *Escherichia coli* of the reference ATCC 35421, called "EC21", in the presence of amoxicillin for N=11.

The same type of experiment carried out on the strain "EC21" resistant to amoxicillin gives the results shown in FIG. 7. No transition is observed and the vast majority of the measured groups is assigned to the "without ATB effect" category. A MIC>8 µg/mL can be assigned to this strain with this test, which is also consistent with the results obtained by the reference method.

Figure 8:
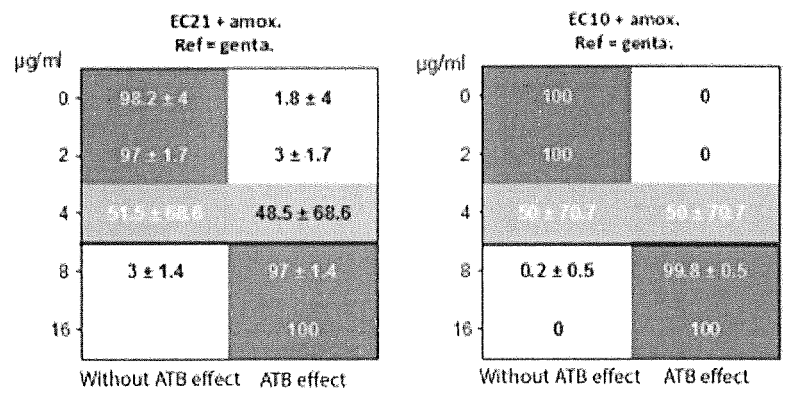
FIG. 8 shows the confusion matrix obtained for the sensitive strain of *Escherichia coli* of the reference ATCC 35421, called "EC21", in the presence of amoxicillin tested with a classifier trained with bacteria exposed to gentamicin for N=11.

As shown in FIG. 8, identical results are obtained by training the classifier on a reference base containing again spectra of bacteria not exposed to antibiotics in order to recognize the "Without ATB effect" class and "Antibiotic effect" spectra of bacteria exposed to a concentration greater than the MIC of another antibiotic molecule belonging to a different family, for example the gentamicin of the previous example.

Similar results to those exposed previously are found. This example proves that it is possible to perform the search for the antibiotic effect of an unknown substance on the bacterial strain tested in this manner and could therefore be applied to the molecule screening.

Example 4: Determination of the Effect of an Unknown Substance on a Bacterial Strain In this example, the aim is to determine the sensitivity phenotype, and to precise a framework for the minimum inhibitory concentration, of a bacterial strain, for example, *Escherichia coli* strains of the reference ATCC 25922 called "EC10", to a substance considered as unknown.

For the needs of the test, a known antibiotic molecule but not belonging to the previously used antibiotic families, is used: ciprofloxacin from the fluoroquinolones family.

The embodiment of the previous example is used for this example.

Only the results obtained for the first 4 concentrations will be explicitly illustrated because an antibiotic effect is rapidly detected for this molecule. A series of N Raman spectra is acquired in each of the chambers from $C_0$ to $C_3$. The used concentrations $c_0$ to $c_3$ are as follows:

$c_0$=0 µg/mL
$c_1$=0.005 µg/mL
$c_2$=0.015 µg/mL
$c_3$=0.064 µg/mL

As previously, the steps carried out for performing the pretreatment of the spectra are as follows:

the removal of saturated spectra
the removal of cosmic rays
the realignment
the extraction of the specific bacterial signal
the removal of deviants
the region of interest and the signal normalization In order to perform a test, an average of N spectra acquired for each tested concentration is made and an average of N spectra of the concentration $c_0$ is subtracted from the result. For the concentration $c_0$, N spectra different from the N spectra used for the subtraction of the reference state are selected. This operation aims at overcoming all variations that are not correlated with the exposure to the antibiotic, under the measurement conditions. A series of 4 test spectra representative of each concentration is thus obtained.

In this example, an unsupervised classification method is used based on the research and the use of at least one spectral signature characteristic of an antibiotic effect. In order to identify this signature, a previously acquired dataset is used for gentamicin and EC10 strain, whose MIC (1 µg/ml) is known for this antibiotic. The dataset is used constituted by the N pretreated spectra acquired on bacteria exposed to one of the concentrations (or more) higher than the MIC in order to extract a characteristic effect. An average of the set of N (or n*N) spectra of the dataset is made and the average of N spectra acquired in the absence of antibiotic is subtracted from the result. This result is described as reference signature. It is this reference signature that is retained to describe the data acquired by exposing bacteria to ciprofloxacin, which is considered as unknown in this case.

Figure 9:
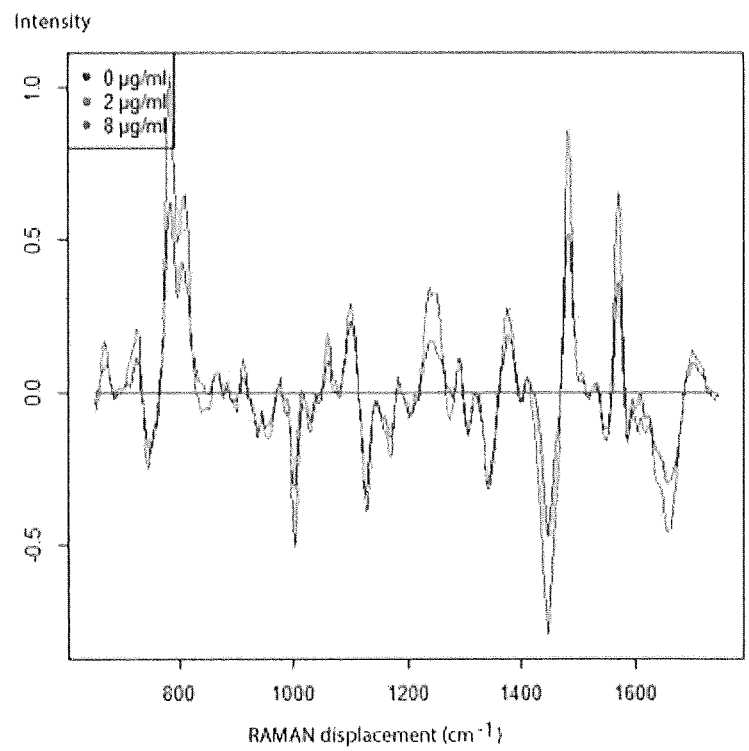
FIG. 9 illustrates the signatures obtained for gentamicin concentrations of 0 μg/mL, 2 μg/mL and 8 μg/m.

The signature set constructed accordingly is shown in FIG. 9. The two signatures obtained for the concentrations $c_1$ and $c_3$ are similar: the same peaks are modified but the intensity is here correlated to the concentration. It should be noted that this difference of intensity could be used to quantify the impact of a given concentration but only in some strain/antibiotic configurations.

The signature extracted from the concentration of 8 µg/mL of gentamicin will be used to analyze the 3 sets of test spectra. In order to do this, the proximity of each test spectrum to the selected signature is evaluated. The evaluation of the distance between the tested spectrum and the signature will be made in this example using a simple Euclidean distance in the space of the spectra but several other distances allow evaluating this proximity (Mahalanobis, L1 . . . ). A threshold is defined empirically with respect to other identical reference experiments carried out previously, the choice of this threshold can be optimized by conventional methods (ROC . . . ) according to the required level of result which can significantly differ between the applications (IVD diagnosis, pharmaceutical screening . . . ). The obtained distance measurement is then compared with this threshold value in order to define the proximity between the retained signature and the difference spectra acquired in the presence of the different concentrations of the molecule considered as unknown. If the distance is below the threshold, the test is positive and an effect of the antibiotic molecule has been detected. If the distance is above this threshold then no effect is detected.

Figure 10:
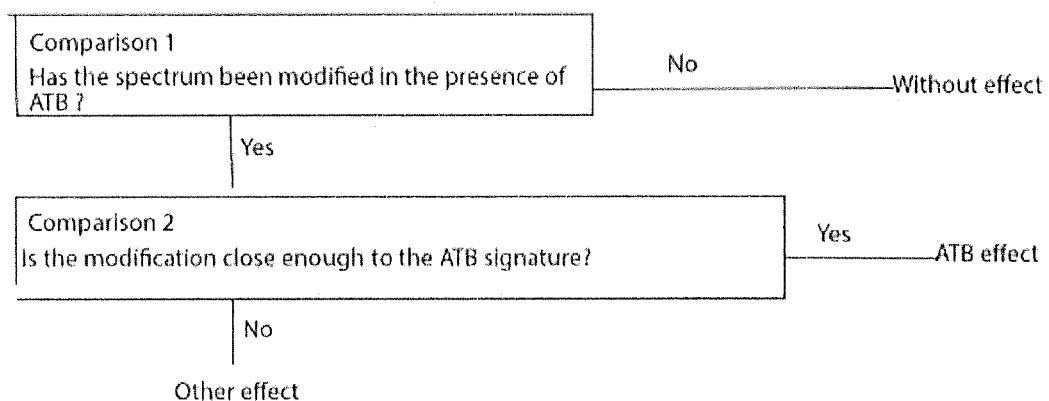
FIG. 10 represents a simplified block diagram provided in the Example 4.

In an advantageous embodiment, it is possible to establish several increasingly strict detection thresholds. In this example, two thresholds are used according to this principle: the first, less strict, allows detecting a significant variation of the tested spectra while the second, stricter, allows describing a great proximity of the modification to the signature. A test of the distance of the tested spectrum to the signature is therefore performed relative to the first threshold. If the test is not passed, then no effect is detected. If the test is passed, the measured distance is below the first threshold, then an effect is detected. A second test is then performed by using the second threshold and if this test is passed, the "Antibiotic effect" result is assigned to the complete test. If this second test is not passed then the "Other effect" result is assigned to the complete test. This configuration allows detecting easily spectral modifications reaching a given concentration but not having sufficient similarity with the reference signature. This configuration therefore simply allows overcoming a portion of the possible hazards occurring during a test (strong inhomogeneity of the capture surface, presence of parasitic particles . . . ). A simplified diagram is shown in FIG. 10.

Another way of performing an equivalent test would be to perform a test by using directly the Euclidean standard or other standard of the tested spectrum and to compare it with a significance threshold chosen threshold in order not to take into account the conventional variations related to the measurement mode (sensor noise level, biological variability . . . ) and then to perform the test at a single strict threshold. If the standard exceeds a certain threshold then the spectrum is significantly different from a near-zero difference spectrum if there were no changes in the concentration and then can be compared strictly to the reference signature, for example by measuring its distance to the signature according to the used standard.

Figure 11:
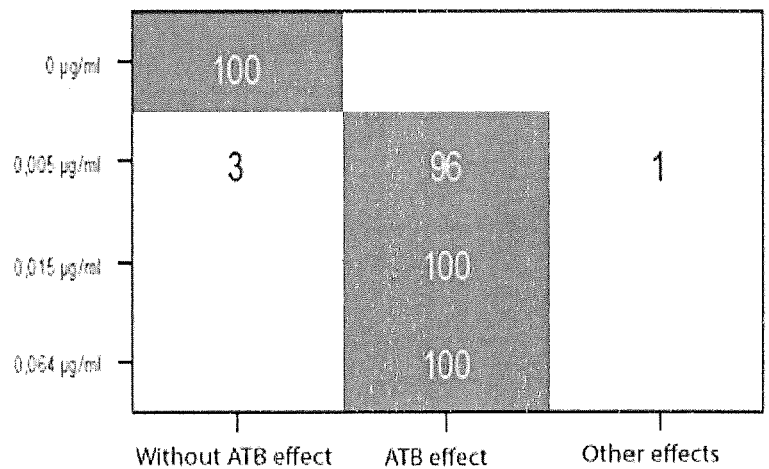
FIG. 11 represents an expression of the reaction of a bacterial strain exposed to different concentrations of ciprofloxacin, obtained according to the method of the invention.

The results obtained are shown in FIG. 11. The detection of an effect for concentrations greater than 0.005 µg/mL is thus observed. An antibiotic effect of ciprofloxacin can therefore be assigned to the strain tested for concentrations greater than 0.005 µg/mL. This test would therefore define a concentration of 0.005 µg/mL as a MIC. A new test could possibly be performed by adding the lowest concentrations between 0 and 0.005 µg/mL if necessary. The EUCAST data for this strain, indicate a known MIC of 0.008 µg/mL and an acceptable variation range of 0.004 µg/mL to 0.016 µg/mL. A test performed with a suitable etest (bioMérieux) allows measuring a MIC of 0.008 µg/mL which confirms that the obtained result is in accordance with the reference methods [BioMérieux products ETEST® CI 32 (antimicrobial susceptibility testing kit; ref. 412311) and VITEK® card N233 (Gram Negative Susceptibility card; ref. 413117)].

Example 5: Application of the Method of the Invention for Determining the Sensitivity Phenotype of the Strain *Staphylococcus Aureus* of the Reference ATCC 25923 Called "SA44" to Oxacillin The retained conditioning device is constituted of two fluidic chambers and two antibiotic concentrations are tested: $c_0$: "Without antibiotic" and "Resistance test".

Let $c_1$ be the concentration of oxacillin: $c_1=8$ µg/mL which corresponds to multiplying by a factor of 32 the concentration of 0.25 µg/mL which corresponds to the clinical breakpoint as defined by the EUCAST. The objective of this test is to determine whether the bacterial strain is considered as resistant according to the definitions provided by the EUCAST.

A solution containing the bacteria to be tested is used as a test sample. This solution is obtained by suspending $5.10^7$ CFU/mL in order to have a concentration potentially encountered in a clinical sample, for example a urine collection. The bacteria can come from a culture in a liquid medium or a culture in agar medium in Petri dish. This bacteria solution is brought into contact with the interface I of the device functionalized by adsorbing polyethylenimine (PEI) (generic capture). After a capture time of 10 minutes allowing the bacteria to come into contact with the functionalization, the interface I is washed with a water solution, this optional step allowing to eliminate the surplus of uncaptured bacteria still in solution. The physiological medium retained in this example is constituted of a poor mixture of BHI Brain Heart Infusion Bouillon (for example of the reference 42081 of bioMérieux) and of PBS 10× (in a 1:9 ratio). After dividing this physiological medium into two fractions, an amount of oxacillin (for example of the reference 00353 of TCI Europe) is added respectively to each of these fractions, allowing to obtain a different concentration of gentamicin $c_0$ or $c_1$. The solutions of concentrations $c_0$ and $c_1$ produced accordingly are respectively introduced into the chambers $C_0$ or $C_1$. The Bacteria captured directly from the sample on the surface I are thus exposed, in a suitable medium, to a different antibiotic concentration depending on the chamber in which they are present.

The device is then heated in order to reach a temperature of 37° C. for two hours and then placed in measurement position on the micro-spectrometer. The marking of the captured bacteria is carried out by an automatic procedure based on image analysis, by a conventional procedure for detecting particles, acquired by means of the micro-spectrometer camera and a suitable light source. This marking allows acquiring automatically a series of Raman spectra ($S_0$ and $S_1$, respectively) acquired on individual bacteria present in each chamber $C_0$ and $C_1$. The number of spectra to be acquired for constituting a dataset depends on the level of requirement on the performances of the tests to be carried out.

As mentioned previously, several methods can be used for treating the obtained data in order to achieve the result. In the present example, a complete method for treating spectra at the individual level is used, comprising a pretreatment step comprising all the phases described above in order to maximize the extraction of a signal of interest and the classification.

In this example, a set of at least 2N spectra extracted from the total set M of the acquired spectra is used: N spectra from $S_0$ and N spectra from $S_1$. These spectra are drawn without replacement among the available M spectra. The average of the N spectra from $S_0$ is subtracted from each of the N spectra from $S_1$ and N spectra from $S_0$, these two batches of spectra constituting a "control test sample" and a "resistance test sample".

For the classification, a reference database is used in the present example, obtained from similar experiments performed previously at dates and from different cultures in order to train a classifier obtained using a Support Vector Machine (SVM) with radial kernel. This classifier is trained to recognize two classes, one "without antibiotic effect" from spectra from conditions without antibiotic and the other "Antibiotic effect" from spectra previously acquired under conditions where the concentration is higher than the MIC of the strain(s) used in the reference base. For each test sample constituted of N difference spectra, these difference spectra are tested individually with respect to the classifier and the majority class for each of the elements of the groups is assigned to the group. This majority assignment is based on the good correlation of the results obtained accordingly with the reference methods but can well be modified in order to take into account some other parameters of the tests. For example, a vote to a threshold different from the majority where as soon as the number of bacteria having no effect exceeds 30%, then a result "Without antibiotic effect" is assigned conservatively. This threshold may also be adjusted in order to take into account the incubation time: thus for example, if the time of exposure to antibiotics is significantly reduced, or if the tested bacterium has a slower typical doubling time, it is necessary to take into account a lower threshold in order to assign an "Antibiotic effect" result to this group of spectra. Finally, a more nuanced system might be adopted where each bacterium is considered in a completely individual way. This last embodiment may be advantageous if the method of the present invention is used for research purposes.

Figure 12:
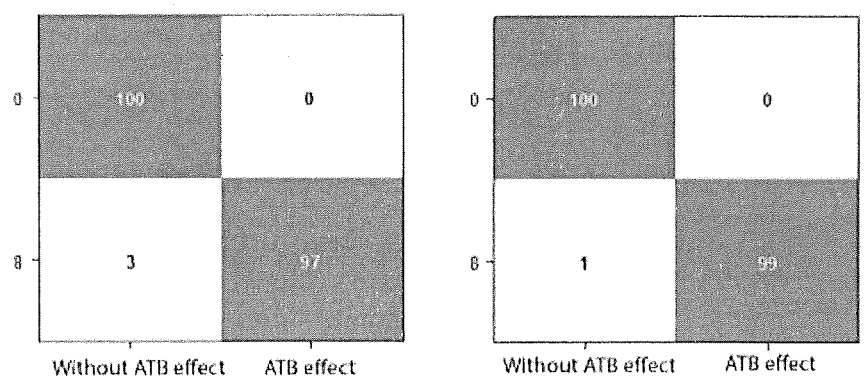
FIG. 12 represents the confounding matrices obtained for the sensitive strain of *Staphylococcus aureus* of reference ATCC 25923, called "SA44", in the presence of oxacillin (MIC=0.25 μg/mL) for N=9 for two experiments, the bacteria being obtained from cultures in a liquid medium.
Figure 13:
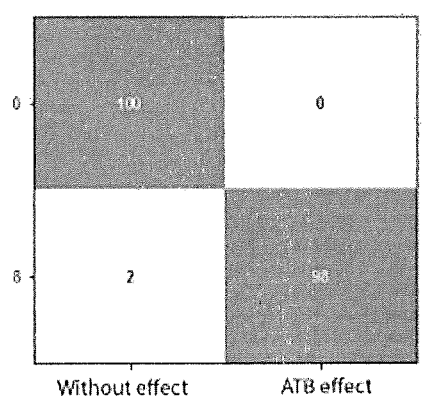
FIG. 13 represents the confusion matrix obtained for the sensitive strain of *Staphylococcus aureus* of the reference ATCC 25923, called "SA44", in the presence of oxacillin (MIC=0.25 μg/mL) for N=9, the bacteria being obtained from cultures in agar medium in Petri dishes.

In order to illustrate the performances obtained accordingly, the average score obtained for all the results that would be obtained with a combination of 9 spectra per concentration (N=9) out of a total set of total acquired spectra, 337 spectra (M=337), is shown in FIGS. 12 and 13.

These matrices show in columns the states "Without ATB effect" and "ATB effect" and in rows the two tested antibiotic concentrations. The score indicates the percentage of the test samples that are assigned to a class given by the classifier described above. Thus, in FIG. 12, it is found that 100% of the samples of N=9 bacteria of the "control test sample" are classified as "Without antibiotic effect" and that a number greater than 97% of the "sensitivity test samples" consisting of bacteria exposed to the test concentration are classified as "ATB effect". The strain can therefore be described as sensitive according to the invention with a high reliability on the basis of only a few individual bacteria analyses. The results observed in these figures are consistent with the reference methods [BioMérieux products ETEST® OX 256 (antimicrobial susceptibility testing kit; ref. 412432) or VITEK® card P631 (Gram Positive Susceptibility card; ref. 414961)] which give as a result a MIC=0.25 µg/mL, which confirms that the bacterial strain is not resistant according to the EUCAST, its MIC not being strictly above the threshold defined by this organism.

The invention claimed is:

1. A method for determining the reaction of at least one bacterium of interest to its exposure to an antibiotic implementing a Raman spectroscopy analysis and comprising the following steps:
    Having a biological sample that could contain said bacteria of interest,
    Preparing at least two fractions of said sample each comprising one or more living bacterium/bacteria of interest,
    Capturing, in each fraction, at least one living bacterium of interest by using a binding partner,
    Exposing at least one of the fractions to at least one concentration of at least one given antibiotic, the other of the fractions being a control fraction,
    Submitting the captured bacterium/bacteria of interest contained in the fractions to an incident light and analyzing the resultant light obtained by Raman diffusion by the captured bacterium/bacteria of interest by Raman spectroscopy in order to obtain as many Raman spectra as bacteria,
    Treating said spectra in order to obtain a signature of the reaction of each bacterium of interest to the exposure of said antibiotic and of the control,
    Comparing the signature obtained for each bacterium of interest to a reference base defined under the same conditions as above for different bacteria and at least said antibiotic, and
    Defining a sensitivity clinical profile of said bacterium of interest to said antibiotic.

2. The method according to claim 1, wherein more than two fractions of said sample are prepared, and at least two fractions are exposed respectively to increasing concentrations of said antibiotic.

3. The method according to claim 1, wherein the concentrations of the antibiotic to which each fraction is exposed is within an interval of values including at least one value selected from values characteristic of an antibiotic/species pair comprising the epidemiological cut-off, the clinical breakpoint(s) or concentration panels used in reference methods.

4. The method according to claim 1, wherein the binding partner is directly or indirectly immobilized on a support.

5. The method according to claim 4, wherein the binding partner interacts specifically with the bacterium/bacteria of interest, and wherein the binding partner is selected from proteins, antibodies, antigens, aptamers, phages, and phage proteins.

6. The method according to claim 1, wherein the captured bacteria are marked and sorted.

7. The method according to claim 1, wherein, before submitting the captured bacterium/bacteria of interest to an incident light, bacteria that have not been captured are eliminated.

8. The method according to claim 7, wherein the bacteria that have not been captured are eliminated before or after the step of exposure to the antibiotic.

9. The method according to claim 1, wherein, after the step of exposure of the fractions, said fractions and the control fraction are concentrated and then subjected to the capture step.

10. The method according to claim 1, wherein the antibiotic is in a physiological medium allowing the bacterium/bacteria of interest to remain alive.

11. The method according to claim 1, wherein the exposure to the antibiotic is performed at a temperature of at least 18° C. and at most 40° C.

12. The method according to claim 1, wherein the exposure to the antibiotic is performed for a time of at least 10 minutes and at most 4 hours.

13. The method according to claim 1, wherein, in order to obtain said signature, for each fraction exposed to the antibiotic, the Raman spectrum/spectra of the control is subtracted from the Raman spectra of each fraction.

14. The method according to claim 1, wherein defining the sensitivity clinical profile of said bacterium of interest to said antibiotic comprises determining the Sensitive, Intermediate or Resistant phenotype of the bacterium of interest to said antibiotic.

15. The method according to claim 14, further comprising determining the minimum inhibitory concentration (MIC) of said antibiotic for said bacterium.

16. The method according to claim 14, wherein each fraction comprises at least 2 bacteria of interest in order to obtain at least 2 signals.

17. The method according to claim 15, wherein each fraction comprises at least 2 bacteria of interest in order to obtain at least 2 signals.

18. The method according to claim 2, characterized wherein the concentration of the antibiotic to which each fraction is exposed is within an interval of values including at least one value selected from values characteristic of an antibiotic/species pair comprising the epidemiological cut-off, the clinical breakpoint(s) or concentration panels used in reference methods.

19. The method according to claim 18, wherein the binding partner is directly or indirectly immobilized on a support.

20. The method according to claim 19, wherein the binding partner interacts specifically with the bacterium/bacteria of interest and wherein the binding partner is selected from proteins, antibodies, antigens, aptamers, phages, and phage proteins.

* * * * *